United States Patent [19]
Kim et al.

[11] Patent Number: 5,936,063
[45] Date of Patent: Aug. 10, 1999

[54] **ANTIMICROBIAL PEPTIDE ISOLATED FROM *BUFO BUFO GARGARIZANS***

[75] Inventors: Sun-Chang Kim, Taejon; Chan-Bae Park, Kyunggi-Do; Dong-Kyun Lee, Taejon; In-Cheol Kim, Gwangju; Seung-Suh Hong, Taejon; Hyun-Soo Lee, Seoul, all of Rep. of Korea

[73] Assignee: Samyang Genex Co., Ltd., Seoul, Rep. of Korea

[21] Appl. No.: 09/051,866

[22] PCT Filed: Aug. 24, 1996

[86] PCT No.: PCT/KR96/00147

§ 371 Date: Apr. 21, 1998

§ 102(e) Date: Apr. 21, 1998

[87] PCT Pub. No.: WO98/07440

PCT Pub. Date: Feb. 26, 1998

[51] Int. Cl.$^6$ ...................................................... A61K 38/00
[52] U.S. Cl. ........................... 530/324; 530/326; 530/333; 530/344; 514/12; 514/13; 514/21; 424/551
[58] Field of Search ................................ 514/12; 530/324, 530/333, 326, 344; 424/551

[56] References Cited

U.S. PATENT DOCUMENTS 3,342,812  9/1967  Komatsu et al. .

FOREIGN PATENT DOCUMENTS 20 26 243 A1  11/1971  Germany .

OTHER PUBLICATIONS

Park, et al., "A Novel Antimicrobial Peptide from Bufo bufo gargarizans", Biochem. Biophys. Res. Commun., 1996, 218, 408–413.

M. Zasloff, *Proc. Nat'l. Acad. Sci., USA,* 84:5449–5453, Aug. 1987.

*Primary Examiner*—Cecilia J. Tsang
*Assistant Examiner*—Fabian A. Jameison
*Attorney, Agent, or Firm*—Darby & Darby

[57] ABSTRACT

The present invention relates to a novel antimicrobial peptide isolated from *Bufo bufo gargarizans* exhibiting therapeutic antibacterial and antifungal properties.

3 Claims, 1 Drawing Sheet

ANTIMICROBIAL PEPTIDE ISOLATED FROM *BUFO BUFO GARGARIZANS*

BACKGROUND OF THE INVENTION

1. Field of the Invention

The present invention relates to a novel antimicrobial peptide isolated from *Bufo bufo gargarizans*, more specifically, to a novel antimicrobial peptide isolated from *Bufo bufo gargarizans* which possesses strong antibacterial and antifungal activities.

2. Description of the Prior Art

Most higher organisms accumulate or secrete antimicrobial peptides as defensive mechanism to protect themselves against pathogenic microorganisms such as virus and bacteria, which also appears in invertebrates including insects. In this connection, studies on the antimicrobial peptides such as Cecropin, an antibiotic peptide isolated from larva of silkworm, have been actively carried out in the art.

Until now, 2,000 or more species of antimicrobial peptides have been discovered, which have different amino acid composition depending on their origin, while they show similar mode of action. These antimicrobial peptides have attracted a considerable attention as new proposed medicines, grounded on the following advantages: first, the antimicrobial peptides have strong activities against broad spectrum of microorganisms, when compared with the conventional antibiotics; secondly, they are potential antibiotics useful for the treatment of human body, since they show antimicrobial activities only against infective pathogens without harmful effect on host cells; thirdly, they can be prepared massively from prokaryotes by the aid of recombinant DNA technology, since all of them do not undergo translational modification such as glycosylation, etc.

Recently, it has been reported that several kinds of antimicrobial peptides exist in skin and stomach of amphibia, some of examplaries are Cecropin, Defensin, Magainin, and Tachyplesin, etc. which consist of 17 to 24 amino acids. They show antimicrobial activities against fungi as well as gram-negative and positive bacteria, and some of them are effective against cancer cell and virus.

Magainin is a famous antibiotic peptide consisting of 23 amino acids, which acts on human pulmonary carcinoma cell as well as pathogenic microoganisms (see: Michael A., Proc. Natl. Acad. Sci. USA, 84:5449–5453 (1987)), and it has been proposed as the most applicable antibiotic peptide now, based on the studies on its antimicrobial activity, mode of action, and structure. In accordance with the present invention, the activities of the antimicrobial peptide of the invention were compared with those of Magainin.

SUMMARY OF THE INVENTION

The present inventors have made an effort to seek novel antibiotic substances from amphibia which have been known to possess a lot of antimicrobial peptides, and isolated a novel antimicrobial peptide from a Korean toad, *Bufo bufo gargarizans*, which shows stronger antibacterial and antifungal activities than any other conventional antimicrobial peptides.

A primary object of the invention is, therefore, to provide a novel antimicrobial peptide isolated from *Bufo bufo gargarizans*.

BRIEF DESCRIPTION OF THE DRAWINGS

The above and the other objects and features of the present invention will become apparent from the following descriptions given in conjunction with the accompanying drawing, in which.

DETAILED DESCRIPTION OF THE INVENTION

Figure 1:
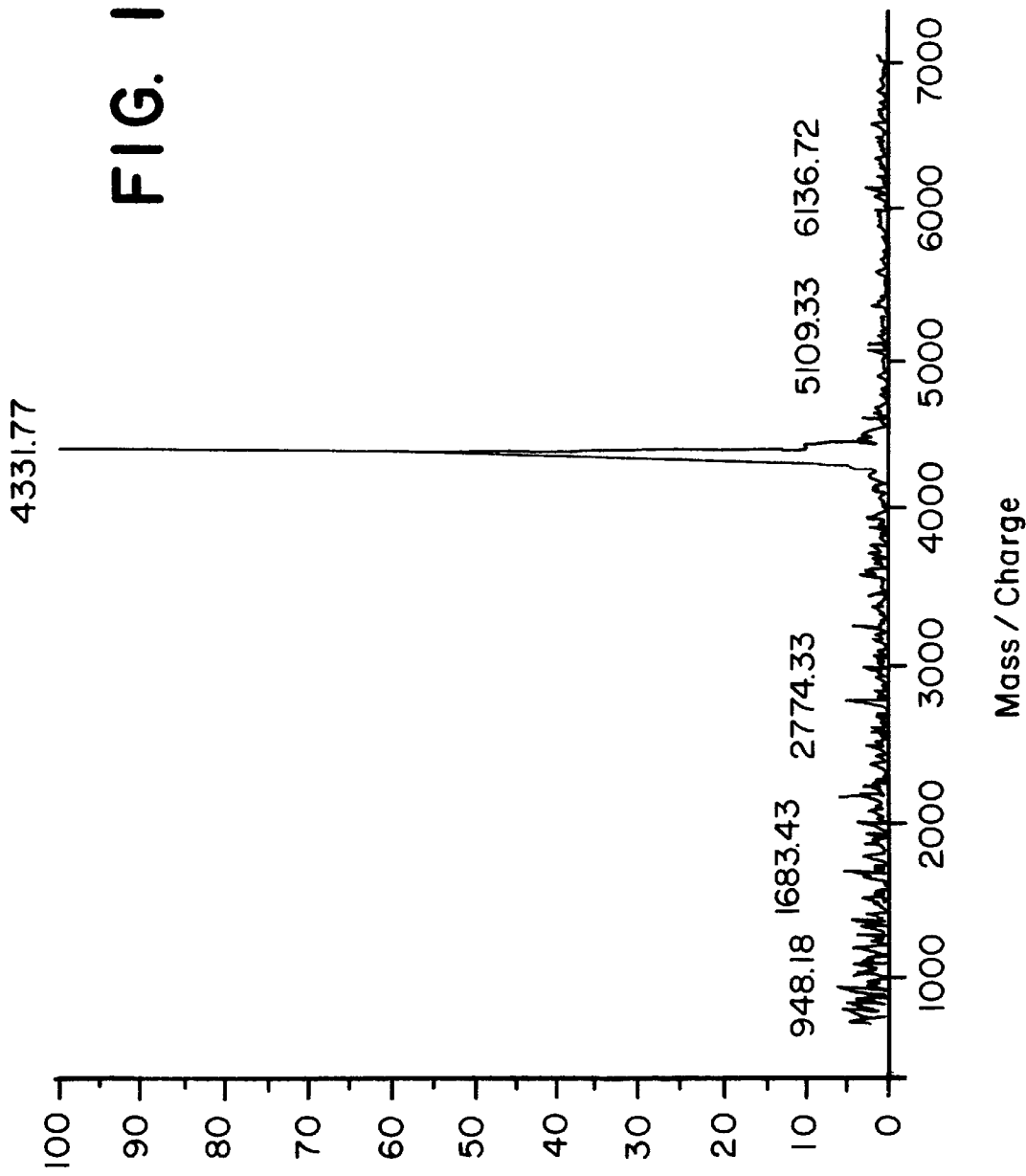
FIG. 1 is mass spectrum which determines molecular weight of the antimicrobial peptide of the invention.

In Korea, *Bufo bufo gargarizans*, a Korean toad has been used as a folk medicine for the treatment of external wound in a dried powder-like formulation. In this connection, the present inventors have screened novel antibiotic substances from the amphibia including *Bufo bufo gargarizans* which has been known to possess a lot of antimicrobial peptides. The present inventors first homogenized stomachs of *Bufo bufo gargarizans*, extracted and concentrated peptides only, and carried out heparin-Sepharose chromatography and $C_{18}$ reverse-phase HPLC (high performace liquid chromatography).

Determination of molecular weight and amino acid sequence of the purified antimicrobial peptide were followed to illucidate that the said peptide has a molecular weight of about 4330 Da and consists of 40 amino acid residues. Also, based on the experiment on antimicrobial activity, it was revealed that it has strong antimicrobial activity against fungi as well as gram-negative and positive bacteria, and higher activity than Magainin which has been known to be the most strong antimicrobial peptide. Moreover, it was also found that a peptide fragment which consists of 22 amino acids obtained by digestion of the antimicrobial peptide with endoproteinase Lys—C had strong antimicrobial activity.

Accordingly, since the antimicrobial peptide of the invention has strong antimicrobial activity against wide range of microorganisms, it can be applied for the development of antimicrobial drug for the treatment of external wound and eye trouble, stimulation of injury care, and oral cleanness.

In describing the antimicrobial peptide of the present invention, the term 'functional equivalents' is employed to mean all peptides substituted by the combinations such as Gly, Ala; Val, Ile, Leu; Asp, Glu; Asn, Gln; Ser, Thr; Lys, Arg; and, Phe, Tyr among the amino acid sequences constituting the antimcrobial peptide.

Further, in describing amino acids of the antimicrobial peptide of the invention, three-letter symbols abbreviated by the IUPAC-IUB standards are employed as followings:

| Amino acid | Symbol |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The present invention is further illustrated in the following examples, which should not be taken to limit the scope of the invention.

EXAMPLE 1: Isolation of an Antimicrobial Peptide from *Bufo bufo gargarizans*

Peptide extraction solution (1M HCl, 1% NaCl, 1% (v/v) trifluoroacetic acid, and 5% (v/v) formate) was added to stomachs of *Bufo bufo gargarizans* asphyxiated with carbon dioxide, and homogenized only to extract peptides. Then, peptides containing fraction thus extracted were concentrated employing Sep-Pak $C_{18}$ cartridge (Waters Associates, USA), and active fractions showing antimicrobial activity were collected employing heparin-Sepharose (Pharmacia, Sweden) chromatography, and $C_{18}$ reverse-phase HPLC (Waters Associates, USA) was followed to purify the titled antimicrobial peptide. In this example, minimal inhibitory concentration (MIC) test was employed to collect the active fractions.

EXAMPLE 2: Characterization of the Antimicrobial Peptide

Example 2-1: Determination of Molecular Weight and Amino Acid Sequence

Molecular weight of the antimicrobial peptide purified in Example 1 was determined as 4330 Da, by the aid of mass spectroscopy (Kartos Kompact MALDI, UK) (see: FIG. 1). Further, amino acid sequence analysis of the said peptide employing automatic amino acid sequencer (Fullerton, USA) revealed that it is a novel peptide consisting of 40 amino acids (SEQ ID No:1) represented as:

```
Ala-Gly-Arg-Gly-Lys-Gln-Gly-Gly-Lys-Val-Arg-Ala-Lys-
Ala-Lys-Thr-Arg-Ser-Ser-Arg-Ala-Gly-Leu-Gln-Phe-Pro-
Val-Gly-Arg-Val-His-Arg-Leu-Leu-Arg-Lys-Gly-Asn-Tyr
```

Example 2-2: Measurement of Antimicrobial Activity of the Peptide

Antimicrobial activity of the peptide of the invention was measured by its minimal inhibitory concentration against various test microorganisms (see: Table 1).

TABLE 1

| Antimicrobial activity of the peptide of the invention | |
|---|---|
| Test microorganism | Minimal inhibitory concentration (µg/µl) |
| Gram-positive bacteria | |
| *Bacillus subtilis* | 22 |
| *Staphylococcus aureus* | 5 |
| *Streptococcus mutans* | 15 |
| Gram-negative bacteria | |
| *E. coli* DH5α | 50 |
| *Serratia marcescens* | 40 |
| *Pseudomonas putida* | 22 |
| *Salmonella typhimurium* | 9 |
| Fungus | |
| *Candida albicans* | 80 |

As can be seen in Table 1, it was determined that the antimicrobial peptide of the invention had strong antimicrobial activity against gram-positive and negative bacteria, and fungi as well, more particularly, they show strong activity against *Staphylococcus aureus*, gram-positive bacterium and *Salmonella typhimurium*, gram-negative bacterium.

On the other hand, comparison of the antimicrobial activity of the peptide with a commercially available Magainin 2 (Sigma, USA) was followed and summarized in Table 2 below.

TABLE 2

| The comparison of the antimicrobial activity of the peptide of the invention with Magainin 2 | | |
|---|---|---|
| | Minimal inhibitory concentration (µg/µl) | |
| Test microorganism | Peptide of the invention | Magainin 2 |
| Gram-positive bacterium *Staphylococcus aureus* | 5 | 13 |
| Gram-negative bacterium *Salmonella typhimurium* | 9 | 25 |

As clearly demonstrated in Table 2, it was found that the peptide of the invention possess stronger activity than Magainin 2 by twofold or more.

Example 2-3: Antimicrobial Activity of a Peptide Fragment

The antimicrobial peptide of the invention was digested with endoproteinase Lys—C (Boehringer Mannheim, Germany) to give several peptides and their antimicrobial activities were examined by minimal inhibitory concentration test employing a test microorganism, i.e., *Bacillus subtilis*. As a result, it was revealed that a peptide fragment which consists of the following 22 amino acids (SEQ ID No:2) had strong antimicrobial activity:

```
Thr-Arg-Ser-Ser-Arg-Ala-Gly-Leu-Gln-Phe-Pro-
Val-Gly-Arg-Val-His-Arg-Leu-Leu-Arg-Lys
```

As clearly illustrated and demonstrated as aboves, the present invention provides a novel antimicrobial peptide isolated from *Bufo bufo gargarizans*. The antimicrobial peptide of the invention consists of 40 amino acid residues, has a molecular weight of about 4330 Da, and shows strong antimicrobial activity against gram-positive and negative bacteria, and fungi as well. Accordingly, it can be applied for the development of antimicrobial drug for the treatment of external wound and eye trouble, stimulation of injury care, and oral cleanness.

SEQUENCE LISTING

<160> NUMBER OF SEQ ID NOS: 3

<210> SEQ ID NO 1
<211> LENGTH: 39
<212> TYPE: PRT
<213> ORGANISM: Bufo bufo gargarizans

<400> SEQUENCE: 1

```
    Ala Gly Arg Gly Lys Gln Gly
Gly Lys Val Arg Ala Lys Ala Lys Thr
    1
    5
    10
    15
    Arg Ser Ser Arg Ala Gly Leu
Gln Phe Pro Val Gly Arg Val His Arg
20
25
30
    Leu Leu Arg Lys Gly Asn Tyr
            35
```

<210> SEQ ID NO 2
<211> LENGTH: 21
<212> TYPE: PRT
<213> ORGANISM: Bufo bufo gargarizans

<400> SEQUENCE: 2

```
    Thr Arg Ser Ser Arg Ala Gly
Leu Gln Phe Pro Val Gly Arg Val His
    1
    5
    10
    15
    Arg Leu Leu Arg Lys
20
```

<210> SEQ ID NO 3
<211> LENGTH:
<212> TYPE:
<213> ORGANISM:

<400> SEQUENCE: 3

This Sequence is intentionally skipp
ed

What is claimed is:

1. An antimicrobial peptide isolated from *Bufo bufo gargarizans* which comprises all or part of following amino acid sequence <SEQ ID NO.: 1> or its functional equivalents:

| | |
|---|---|
| Ala-Gly-Arg-Gly-Lys-Gln-Gly-Gly-Lys-Val-Arg-Ala- | 12 |
| Lys-Ala-Lys-Thr-Arg-Ser-Ser-Arg-Ala-Gly-Leu-Gln- | 24 |
| Phe-Pro-Val-Gly-Arg-Val-His-Arg-Leu-Leu-Arg- | 36 |
| Lys-Gly-Asn-Tyr. | 40 |

2. An antimicrobial peptide derived from the antimicrobial peptide of claim 1 which comprises following amino acid sequence <SEQ ID NO.: 2> or its functional equivalents:

| | |
|---|---|
| Thr-Arg-Ser-Ser-Arg-Ala-Gly-Leu-Gln-Phe-Pro- | 11 |
| Val-Gly-Arg-Val-His-Arg-Leu-Leu-Arg-Lys. | 22 |

3. An antimicrobial drug which comprises the peptide of claim 1 as active ingredient and pharmaceutically acceptable carrier.

* * * * *